US012214072B2

(12) United States Patent
Raz (10) Patent No.: US 12,214,072 B2
(45) Date of Patent: Feb. 4, 2025

(54) CHEWABLE TABLET AND METHOD OF PREPARING THE SAME (71) Applicant: AMBROSIA SUPHERB LTD., Natanya (IL)

(72) Inventor: Sharon Raz, Givat Ela (IL)

(73) Assignee: AMBROSIA SUPHERB LTD., Natanya (IL)

( * ) Notice: Subject to any disclaimer, the term of this patent is extended or adjusted under 35 U.S.C. 154(b) by 147 days.

(21) Appl. No.: 17/284,984

(22) PCT Filed: Nov. 4, 2019

(86) PCT No.: PCT/IL2019/051205
§ 371 (c)(1),
(2) Date: Apr. 13, 2021

(87) PCT Pub. No.: WO2020/089921
PCT Pub. Date: May 7, 2020

(65) Prior Publication Data
US 2021/0346286 A1 Nov. 11, 2021

(30) Foreign Application Priority Data
Nov. 4, 2018 (IL) .......................... 262768

(51) Int. Cl.
A61K 9/68 (2006.01)
A61K 9/20 (2006.01)
A61K 9/28 (2006.01)
A61K 31/07 (2006.01)
A61K 31/355 (2006.01)
A61K 31/375 (2006.01)
A61K 31/4188 (2006.01)
A61K 31/4415 (2006.01)
A61K 31/455 (2006.01)
A61K 31/51 (2006.01)
A61K 31/519 (2006.01)
A61K 31/525 (2006.01)
A61K 31/593 (2006.01)
A61K 31/714 (2006.01)
A61K 33/10 (2006.01)
A61K 33/24 (2019.01)
A61K 33/26 (2006.01)
A61K 33/30 (2006.01)
A61K 33/32 (2006.01)
A61K 36/481 (2006.01)
(Continued)

(52) U.S. Cl.
CPC .......... A61K 9/0058 (2013.01); A61K 9/2018 (2013.01); A61K 9/286 (2013.01); A61K 9/2866 (2013.01); A61K 9/2886 (2013.01); A61K 9/2893 (2013.01); A61K 31/07 (2013.01); A61K 31/355 (2013.01); A61K 31/375 (2013.01); A61K 31/4188 (2013.01); A61K 31/4415 (2013.01); A61K 31/455 (2013.01); A61K 31/51 (2013.01); A61K 31/519 (2013.01); A61K 31/525 (2013.01); A61K 31/593 (2013.01); A61K 31/714 (2013.01); A61K 33/10 (2013.01); A61K 33/24 (2013.01); A61K 33/26 (2013.01); A61K 33/30 (2013.01); A61K 33/32 (2013.01); A61K 36/481 (2013.01); A61K 36/484 (2013.01); A61K 36/9068 (2013.01)

(58) Field of Classification Search
CPC .... A61K 9/0058; A61K 9/2018; A61K 31/07; A61K 31/355; A61K 31/375; A61K 31/4188; A61K 31/4415; A61K 31/455; A61K 31/51; A61K 31/593; A61K 31/714; A61K 36/9068; A61K 9/286; A61K 9/2866; A61K 9/2886; A61K 9/2893; A61K 31/519; A61K 31/525; A61K 33/10; A61K 33/24; A61K 33/26; A61K 33/30; A61K 33/32; A61K 36/481; A61K 36/484; A61K 9/205; A61K 9/2054; A61K 47/36; A23G 4/043; A23G 4/126; A23L 33/10; A23L 33/15; A23P 10/28
See application file for complete search history.

(56) References Cited

U.S. PATENT DOCUMENTS

| 5,433,960 | A | 7/1995 | Meyers |
| 5,589,191 | A | 12/1996 | Ukigaya et al. |
| 6,551,634 | B2 | 4/2003 | Joergensen |
(Continued)

FOREIGN PATENT DOCUMENTS

| CN | 1366878 | 9/2002 |
| CN | 101179944 | 5/2008 |
(Continued)

OTHER PUBLICATIONS

International Search Report and Written Opinion of the International Searching Authority, issued Feb. 18, 2020 in corresponding International Patent Application No. PCT/IL2019/051205.

Primary Examiner — Frederick F Krass
Assistant Examiner — Lucy M Tien
(74) Attorney, Agent, or Firm — GREENBERG TRAURIG, LLP (57) ABSTRACT The present disclosure provides chewable tablets comprising (i) a compressed core including a bioactive molecule; (ii) a protective layer over said compressed core, and (iii) one or more soft-coating layers over said protective layer, each soft coating layer comprises gum base powder; wherein the protective layer comprises water-insoluble cellulose based polymers, preferably ethyl cellulose based polymer.

22 Claims, 7 Drawing Sheets (51) Int. Cl.
*A61K 36/484* (2006.01)
*A61K 36/9068* (2006.01)

(56) References Cited

U.S. PATENT DOCUMENTS

| | | | |
|---|---|---|---|
| 8,603,440 B2 | 12/2013 | Andersen et al. | |
| 8,722,022 B2 | 5/2014 | Andersen et al. | |
| 2001/0053397 A1 | 12/2001 | Joergensen | |
| 2002/0119196 A1* | 8/2002 | Parikh | A61P 29/00 |
| | | | 514/290 |
| 2004/0194793 A1 | 10/2004 | Lindell et al. | |
| 2006/0039872 A1 | 2/2006 | Schmidt | |
| 2006/0051455 A1 | 3/2006 | Andersen et al. | |
| 2007/0098746 A1* | 5/2007 | Nichols | A61K 31/485 |
| | | | 424/490 |
| 2007/0141198 A1* | 6/2007 | Yang | A23G 3/54 |
| | | | 426/3 |
| 2010/0203190 A1* | 8/2010 | Barkalow | A23L 29/37 |
| | | | 426/103 |
| 2011/0070287 A1 | 3/2011 | Nielsen et al. | |
| 2011/0104239 A1 | 5/2011 | Knutsen et al. | |
| 2011/0117173 A1 | 5/2011 | Hummeluhr et al. | |
| 2016/0120802 A1* | 5/2016 | Sun | A61K 9/0056 |
| | | | 514/529 |
| 2016/0296474 A1 | 10/2016 | Romanoschi et al. | |
| 2016/0303042 A1 | 10/2016 | Yoshimura et al. | |
| 2017/0224671 A1 | 8/2017 | Nielsen | |
| 2017/0367975 A1 | 12/2017 | Topsoe et al. | |

FOREIGN PATENT DOCUMENTS

| | | |
|---|---|---|
| JP | 5836037 | 11/2015 |
| RU | 2291688 | 1/2007 |
| RU | 2355183 | 5/2009 |

\* cited by examiner

CHEWABLE TABLET AND METHOD OF PREPARING THE SAME

TECHNOLOGICAL FIELD

The present disclosure relates to chewable tablets for oral delivery of bioactive molecules and their preparation method.

BACKGROUND ART

References considered to be relevant as background to the presently disclosed subject matter are listed below:
International Patent Application Publication No. WO09080020 (corresponding to U.S. Pat. No. 8,722, 022)
International Patent Application Publication No. WO09080022 (corresponding to U.S. Pat. No. 8,603, 440)
International Patent Application Publication No. WO10008879 (corresponding to US2011/0104239)
International Patent Application Publication No. WO13091631 (corresponding to US2017/224671)
U.S. Pat. No. 6,551,634
International Patent Application Publication No. WO10003425 (corresponds to US2011/117173)
Japanese Patent No. 5836037
International Patent Application Publication No. WO17105564 . . .
US Patent Application Publication No. 2016296474
US Patent Application Publication No. 2006039872
US Patent Application Publication No. 2001053397
International Patent Application Publication No. WO9320708

Acknowledgement of the above references herein is not to be inferred as meaning that these are in any way relevant to the patentability of the presently disclosed subject matter.

BACKGROUND

Gum base material is commonly used for the delivery of substances of interest.

For example, WO09080020 describes a method of dosing pharmaceutical active ingredients in a compressed chewing gum tablet.

WO09080022 describes compressed chewing gum tablets comprising one or more pharmaceutically active ingredients and one or more enhancers, wherein the chewing gum tablet comprises at least one chewing gum module comprising a chewing gum composition, and wherein the chewing gum composition comprises chewing gum granules containing gum base, and wherein said enhancers are at least partly contained within at least a part of said chewing gum granules.

WO10008879 describes an extruded, centre-filled or coated confectionary material which contains a probiotic which is capable of having a shelf life greater than about six months as well as a production method thereof.

WO13091631 describes the delivery of nicotine from a compressed chewing gum tablet that comprises two modules; a first module comprising nicotine and tablet material, and a second module comprising gum base and nicotine.

U.S. Pat. No. 6,551,634 describes a method of producing a chewing or bubble gum piece and a chewing or bubble gum piece, the gum piece has a core which may contain flavoring, a mixture of flavoring and medicine or all medicine, and the core is encapsulated with an intermediate layer which is free from gummy mass, the latter is in turn encapsulated with an outer layer. The intermediate layer separates the core from contact with outer layer.

WO10003425 describes a powdered chewing gum composition and a chewing gum comprising a core and one or more layers of the chewing gum composition. The chewing gum is referred to as a centre-filled chewing gum. One or more intermediate compartments comprising the chewing gum composition may be used as a glue.

JP 5836037 describes a multilayered aroma containing chewing gum.

WO17105564 describes a chewing gum comprising powdered gum base combined with caffeine and L-theanine that may include layers.

US Patent Application Publication No. 2016296474 describes an oral, chewable dosage forms that are suitable for delivery of one or more active ingredients to a consumer, particularly a human individual. The dosage forms is configured as multicomponent compositions formed of a first component including a gummy composition; a second component that is a particulate material or is a pre-formed solid unit or plurality of pre-formed solid units; and an active ingredient.

US Patent Application Publication No. 2006039872 describes a layered chewing gum tablet that comprises at least one layer containing 35.5-86.5 w % of gum base, based on the total weight of the layered chewing gum tablet. The gum base is present in compressed gum granules having an average diameter in the range of 0.1 to 2.5 mm.

US Patent Application Publication No. 2001053397 describes a method of producing a chewing or bubble gum piece and a chewing or bubble gum piece that has a core which may contain flavoring, a mixture of flavoring and medicine or all medicine. The core is encapsulated with an intermediate layer which is free from gummy mass. The intermediate layer is encapsulated with an outer layer which is an outer layer of a gum piece that is placed in the mouth of a person chewing the gum which contains gummy mass. The intermediate layer separates the core from contact with outer layer.

Finally, International Patent Application Publication No. WO9320708 describes a method of prolonging the shelf life of stick chewing gum, and a shelf-stable chewing gum prepared according to the method. Specifically, a chewing gum sheet is coated on both sides with an aqueous solution of an edible film forming agent which, when partially dried, serves as an adhesive. A layer of wax is then applied to each of the layers of edible film forming agent.

GENERAL DESCRIPTION

The present disclosure provides, in accordance with a first of its aspects, a chewable tablet comprising (i) a compressed core including a bioactive molecule; (ii) a protective layer over said compressed core; and (iii) one or more soft coating layers over the protective layer comprising gum base powder; wherein said protective layer comprises a water insoluble cellulose-based polymer.

In a preferred embodiment, the water insoluble cellulose based polymer comprise or are ethyl cellulose (EC) polymers, also known by the trademark name Ethocel™.

In accordance with a further aspect, the present disclosure provides a method of preparing a chewable tablet comprising:
(a) applying onto a compressed tablet comprising a bioactive molecule a protective material comprising a water insoluble cellulose based polymer, to form a protective coating over said compressed tablet;

(b) applying one or more soft-coating layers onto said protective coating, said soft coating layers comprise gum base powder.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIGS. 1A-1B provide schematic illustrations of the tablet and the different layers, FIG. 1A illustrating the core of the tablet, a protective layer and the soft coating over the protective layer, while FIG. 1B illustrates additional layers over the soft coating.

FIG. 3A is an image at time point t=0, FIG. 3B is an image at time point t=4 hours and FIG. 3C is an image at time point t=18 hours.

FIG. 6A is an image of tables (core tablet #2 in Table 1) with HPMC protective coating at time t=0, FIG. 6B is an image of the beaker of FIG. 6A, after 40 minutes; FIG. 6C is an image of tablets with carnauba wax at t=0 and FIG. 6D is an image of the beaker of FIG. 6C after 20 minutes; FIG. 6E is an image of tablets with Bees wax coating.

DETAILED DESCRIPTION

The present disclosure is based on the need to improve integrity of gum coated chewable tablets. Specifically, tablets combined with gum base material were found to significantly crack in time (during storage), resulting in a damaged and commercially inferior product.

With the aim of, inter alia, overcoming cracking of gum coated chewable tablets, a protective coating over the tablet has been developed and introduced into chewable tablets in a manner that unexpectedly improved the stability of gum coated tablets, by essentially preventing cracking of the outer coating of the product.

Specifically, a chewable tablet has now been developed that comprises a core that comprises or is a compressed tablet including a bioactive molecule; and a protective coating over the core, sealing said compressed core from the outer environment (sandwiched between the compressed tablet and the gum-containing coating). More specifically, over the protective coating there is a soft-coating/gumming coating comprising one or more gum base powder layers, and optionally other materials, such as a soft coating binder and oil based material, as further discussed below.

It has been found that by the specific selection of a water insoluble polymers to be included in the protective coating, out of various other possible water insoluble polymers that are commercially available and commonly used in the industry, allowed for the significant elimination of cracks being formed, which were present with other insoluble polymers.

As will be further discussed below, the cellulose based polymers are preferably ethyl cellulose based polymers or predominantly comprise EC based polymers. In this context, when referring to a protective coating that predominantly comprise EC polymers it is to be understood to the coating may comprise other polymers, or other water insoluble polymers, as long as the amount of the EC polymers out of the total amount of polymers in the protective coating is not less than 40% by weight; at times, not less than 50%; at times, not less than 60% by weight; at times, not less than 70% by weight; at times, not less than 80% by weight; at times, not less than 90% by weight; at times, not less than 95% by weight, or even not less than 98% by weight.

In the context of the present disclosure, when referring to cracks in the outer surface/coating of the tablet it is to be understood as encompassing any defect or recess in the continuity of the outer surface. The crack can be in the form of an elongated fracture or slit or in the form of one or more apertures distributed on the surface, etc., the crack can be of any dimension or depth and if more than one crack appears on the surface, the different cracks can have different sizes and shapes.

In the context of the present disclosure, the protective coating prevents the formation of even a single crack.

In the context of the present disclosure, a crack is one that can be viewed by the inspecting eye. Thus, it may be that a tablet as disclosed herein could include a level of discontinuity in the outer surface that is not seen by the inspecting eye but could be observed by magnifying tools.

Further, in the context of the present invention, the protective coating provides stability of the tablet when brought into contact with water or moisture.

The compressed core is a compressed tablet that comprises at least one bioactive material and optionally a filler material.

In the context of the present disclosure, the filler within the compressed core is typically an inert substance, and is one that is known in the tablet industry and as such should not be considered as a limiting element of the tablet disclosed herein.

As to the bioactive material, it is to be understood as one that has a beneficiary effect on the subject's well-being, e.g. stimulates a beneficial response from the body, as further discussed below.

In the context of the present disclosure, bioactive compounds are natural molecules obtained from plants, animals, marine organisms etc., that are capable of modulating metabolic processes and resulting in the promotion of better health. Without being bound thereto, they can exhibit beneficial effects such as antioxidant activity, inhibition or induction of enzymes, inhibition of receptor activities, and induction and inhibition of gene expression.

There is a variety of possible bioactive materials that can be incorporated into the tablet's core. For example, and without being limited thereto, the tablet may carry vitamins, such as Vitamin C, Folic Acid, B12 and more; Minerals such as, Zinc, Iron, Calcium and more; Herb such as, Cranberries, Ginger and more.

The compressed core is a hard compressed tablet. Hardness can be determined by conventional tablet hardness testing techniques as known in the art.

As appreciated, hardness of a tablet reflects the breaking point and structural integrity of the tablet "under conditions of storage, transportation, and handling before usage". If the tablet is 'too hard', it may fail to disintegrate in the required period of time and will fail dissolution tests; if the tablet is 'too soft' it may fail to withstand handling during subsequent processing such as coating or packing and shipping operations.

The hardness of the core tablet, can be measured by any conventional Tablet Hardness Tester, such as, without being limited thereto "VanderKamp® VK 200". In some embodiments, the hardness of the core tablet is in the range of between 4-20 kiloponds (kp), at times between 5-15 kp, at times between 8-14 kp, at times between 8 to 20 kp and further at times, between 9-12kp, each range constituting a separate embodiment of the present disclosure.

The compressed tablet core is coated with a protective coating. This protective coating over the tablet's core comprises one or more thin layers, each layer comprises at least a water insoluble cellulose based polymers. Typically, the protective coating is sprayed over the tablet's core until a unified homogenous coat is formed over the core tablet. It is appreciated that such sprayed coating has a thickness of very few microns.

In some embodiments, the protective coating comprises a water insoluble non-swellable cellulose based polymers.

In some embodiments, the protective coating comprises a non-biodegradable polymers.

In some embodiments, the protective coating comprises ethyl cellulose (EC), i.e. the water insoluble polymers is or comprises EC polymers.

According to some examples, the EC is one having % ethoxy groups of between 45-55% at times, 48.5-50% or one having 48.0-49.5% such as that produced by Aqualon (EC-10) or that having the CAS number 9004-57-3.

Notably, other water insoluble cellulose based polymers have been examined (hydroxypropyl methylcellulose exemplified herein) and it has been surprisingly found that EC polymers provide the best result in terms of tablet stability.

In some embodiments, the protective coating comprises or consists essentially of ethyl cellulose and optionally includes residual organic solvent.

When referring, in the context of the present disclosure, to "residual" amounts, it is to be understood as an amount that while being detectable by analytical tools, has insignificant or no effect on the integrity of the tablet and/or no effect on the entity consuming the tablet. In some embodiments, the "residual" amount is no more than 3% w/w out of the total weight of the final product (tablet and at least the protecting coating).

The protective coating is covered by a soft, gum base, coating (referred to at times as the "gumming coating"). The soft coating comprises at minimum gum base powder.

The gum base powder can be any known, commercially available, gum base powder that is typically used in the gum industry.

In some embodiments, the soft coating comprises a soft coating binder to bind the powder to the compressed tablet. The soft coating binder can be any binder typically used in the gum industry.

In some embodiment, the soft coating binder comprises a combination of a sugar based material and gum Arabic (*Acacia* gum).

In some embodiments, the sugar based material is any one of sugar, sugar substitutes, sugar alcohols and any combination of same.

In some embodiments, the soft coating binder comprises one or more sugar alcohols.

In some embodiments, the sugar alcohol is selected from the group consisting of Ethylene glycol (2-carbon), Glycerol (3-carbon), Erythritol (4-carbon), Threitol (4-carbon), Arabitol (5-carbon), Xylitol (5-carbon), Ribitol (5-carbon), Mannitol (6-carbon), Sorbitol (6-carbon), Galactitol (6-carbon), Fucitol (6-carbon), Iditol (6-carbon), Inositol (6-carbon; a cyclic sugar alcohol), Volemitol (7-carbon), Isomalt (12-carbon), Maltitol (12-carbon), Lactitol (12-carbon), Maltotriitol (18-carbon), Maltotetraitol (24-carbon) and Polyglycitol.

Each of the above sugar alcohol and any combinations thereof constitutes a separate embodiment of the present disclosure.

In some embodiments, the soft coating binder comprises one or more sugar substitutes.

In some embodiments, the sugar substitute (that is not a sugar alcohol) is selected from the group consisting of Erythritol, Fructooligosaccharide, Glycyrrhizin, Glycerol, Hydrogenated starch hydrolysates, Inulin, Isomaltooligosaccharide, Isomaltulose, Mabinlin, Maltodextrin, Miraculin, Monatin, Monellin, Osladin, Pentadin, Polydextrose, Psicose, Tagatose and Thaumatin.

Each of the above sugar substitutes (and sugar alcohols) and any combinations thereof constitutes a separate embodiment of the present disclosure.

In some embodiments, the sugar alcohol comprises at least or is isomalt.

In some embodiments, the sugar substitute comprises at least or is Maltodextrin.

In some embodiments, the soft coating binder comprises gum Arabic.

There are various types of gum Arabic that can be used within the soft coating binder, in accordance with the present disclosure.

Gum Arabic, also known by the term *acacia* gum (identified by the European food safety authority by the E number E414) is a water soluble type of fibers that is obtained, for example, as exudates of hardened sap taken from mainly two species of the *Acacia* trees belonging to the Fabaceae family: *Acacia* Senegal and *Acacia* Seyal, although over a hundred of species of *Acacia* are known. *Acacia* gum is an edible biopolymer comprised of a complex mixture of carbohydrates (complex glycoproteins and polysaccharides by a high proportion of carbohydrates (~97%), which are predominantly composed of D-galactose backbone and side chains of D-glucuronic acid with terminal L-rhamnose or L-arabinose units and a low proportion of proteins (<3%)), having a low glycemic index and prebiotic effect (i.e., non-digestible fiber compounds that stimulate growth and/or activity of advantageous bacteria). The molecular weight of Acacia gum is between 200 and 600 kDa. *Acacia* gum is non-digestible in the human intestine and is used in the food industry as a stabilizer (E414). In some embodiments *Acacia* gum is obtained commercially.

In some embodiments, the gum Arabic is one derived from *Acacia* Seyal tree or *Acacia* Senegal tree. Other sources of gum Arabic may be *Acacia* Bussei, *Acacia* Drepanolobinn, *Acacia* Mellifera, *Acacia* Nilotica and *Acacia* Tortilis. Once the soft (chewing gum) coating is applied, this is then coated with a hard coating, providing the tablet with a crust, crunchy, cover.

The gum containing soft coating over the protective coating is composed of several layers of the gum base powder, each layer being adhered to each other and to the compressed tabled by the use of the soft coating binder. Notably, while typically each layer is bound to its preceding layer by the same binder composition, it may be that different binder compositions are used to adhere different layers of the gum base powder, e.g. different sugar based materials mixed with the gum Arabic.

In some embodiments, the gum containing soft coating comprises at least 5, at times at least 10 and at times, at least 15 thin layers of the gum base powder. In some embodiments, this gum containing coating contains between 5 to 30 thin layers of the gum base powder, in some other embodiments, the gum containing coating comprises between 10 to 30 layers, and in some further embodiments, the gum containing soft coating comprises between 15 to 25 layers. As noted above, these thin layers are a combination of such gum base powder and the suitable soft coating binder therebetween, the layers of the gum base powder being applied and adhered layer by layer until reaching a desired thickness of the gum-containing soft coating.

In some embodiments, the soft coating includes other elements, such as oil based agents. The oil based agents are at least applied, as intermediate layers between two, but not necessarily all, gum base containing layers. For example, the soft coating may contain 20 layers of the gum base powder, and every 3 layers of the gum base powder, there will be a thin layer (sprayed layer) of an oil based agent.

In some embodiments, the oil based agents, are also added to the soft coating binder (the mixture of the gum Arabic and sugar based material).

In some embodiments, the oil based agent is an oil based flavoring agent. Without being limited thereto, the oil based flavoring agent is one or a combination selected from the group consisting of medium chain triglycerides (MCT) oil, coconut, corn, palm oils and triacetin.

In some embodiments, the gum containing soft coating comprises a combination of layers of gum base powder, binder, and oil based flavoring agent(s).

As will be further shown below, the inclusion of oil based flavoring agents in between the layers of the soft coating significantly improved the qualities of the resulting chewable tablet in terms of, inter alia, its chewability. Specifically, the resulting tablet was softer and more stretchable (after chewing, it was easier to manually stretch the gum.

The soft coating is then covered with a hard coating (in some cases providing the chewable tablet with a crust or crust like coat).

In some embodiments, the hard coating comprises a mixture of gum Arabic and a sugar based material (a single or combination of sugar based compounds), referred to herein by the term "hard coating binder".

In some embodiments, the hard coating binder comprises the same sugar based material from which the binder in soft coating is composed.

In some embodiments, the hard coating binder comprises the gum Arabic from which the binder in soft coating is composed.

In yet some further embodiments, the hard coating binder comprises the gum Arabic and sugar based material from which the binder in soft coating is composed. In accordance with this embodiment, the ratio between the gum Arabic and the sugar based material or the Brix of the hard coating binder may be different from that of the soft coating binder.

In some embodiments, the hard coating includes other ingredients, such as emulsifier and/or thickening agent, and/or pigments (e.g. titanium dioxide), etc.

In some embodiments, the hard coating comprises at least titanium dioxide (in a mixture with the gum Arabic and the sugar based material).

The hard coating is composed of several thin layers of the hard coating binder.

In some embodiments, the hard coating comprises at least 5, at times at least 10 and at times, at least 15 thin layers of the hard coating binder, namely, the mixture of the sugar based material and gum Arabic (and optionally other ingredients). The additional ingredients, such as the pigments may be included in each layer, or may be included in the outer layers of the hard coating.

In some embodiments, this hard coating contains between 5 to 30 thin layers of the hard coating binder, in some other embodiments, the hard coating comprises between 10 to 30 layers, and in some further embodiments, the hard coating comprises between 15 to 25 layers of the hard coating binder.

The manner of applying the layers of the soft coating and the layers of the hard coating are further described below.

In some embodiments, an additional color coating is applied over the hard coating.

The coated tablet may then be provided with a polish, as typically applied to gum coated tablets to impart a shiny/glossy distinctive appearance to the tablet. Polishing can be provided by any means and with any material known in this art, and typically is applied within a polishing pan (drum coater).

In some embodiments, the polish is provided by applying onto the hard coat a wax based material.

Without being limited thereto, the polish coat comprises one or a combination of materials selected from the group consisting of microcrystalline wax, carnauba wax, candelila wax, beeswax and hard paraffin, each constituting a separate embodiment of the present disclosure.

Figure 1A:
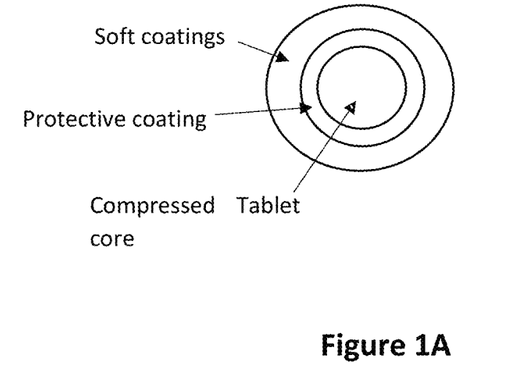
Figure 1B:
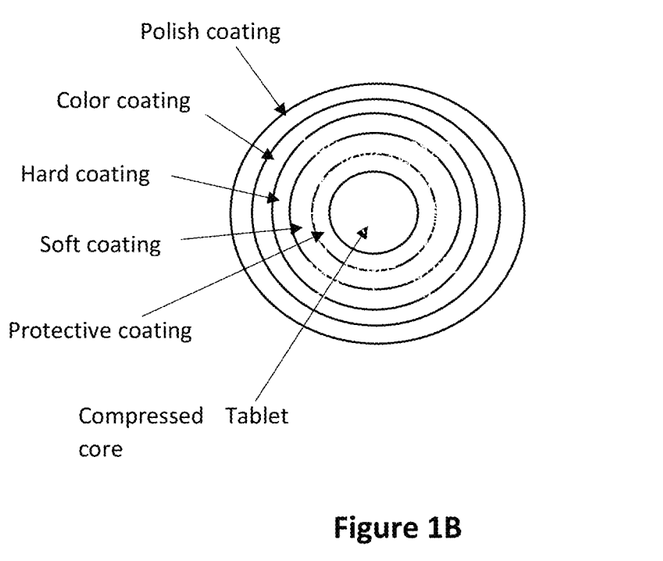

FIGS. 1A-1B provide illustrations of the different coats over the compressed tablet that form the chewable tablet in accordance with a non-limiting embodiment of the present disclosure. Specifically, FIG. 1A illustrates a compressed core, coated with a protective layer and thereon with a soft coating, while FIG. 1B shows the different coatings, and their order over the compressed core (the most outer layer being the polish coat, to the most inner compressed tablet core).

The chewable tablets are produced by a method which constitutes an additional aspect of the present disclosure.

According to the present disclosure, the method comprises at minimum the following steps:
    applying onto a compressed tablet comprising a bioactive molecule a protective material comprising a water insoluble polymer, to form a protective coating over said compressed tablet;
    applying one or more soft-coating layers onto said protective coating, said soft coating layers comprise at least gum base powder, preferably a combination of gum base powder and a soft coating binder.

In some embodiments, the application of the protective material over the tablet's core comprises dissolving the water insoluble polymer, as defined hereinabove, in an organic solvent and spraying the dissolved polymer over the compressed tablet.

The organic solvent is, in accordance with some embodiments, a polar solvent.

In some embodiments, the solvent is a polar protic solvent.

In some embodiments, the solvent is an alkanol, specifically $C_nH_{2n}OH$.

In some embodiments, the organic solvent is ethanol, preferably ethanol 99%.

After spraying the tablet core with the protective material, the organic solvent is allowed to evaporate. It is noted that while it is desired to remove all organic solvent before proceeding, some residual amount of the organic solvent may remain in the compressed core, during the subsequent coating stages.

Onto the protective coating a soft coating is then applied. The soft coating is composed of layers of gum base powder, being applied sequentially and alternately with a soft coating binder. In other words, before each application of a dry gum base powder, the tablet is wetted with an aqueous solution of the soft coating binder.

In some embodiments, the wetting of the tablets with the soft coating binder and subsequent spreading of the gum base powder over the wet tablets is by spinning of the tablets within a drum.

The soft coating binder solution comprises the soft coating binder components described hereinabove, dissolved in water.

In some embodiments, the soft coating binder solution comprises a sugar based material and gum Arabic.

In some embodiments, each layer of the soft (gum base powder) coating is dried prior to adding a next layer of a soft coating. Before applying the next layer of the powder, the dried coated tablets are wetted with the soft coating binder solution which spinning in the drum, and only when sufficiently wet, the dry powder is inserted into the spinning drum.

Each soft coating layer may be the same or different in composition. In some embodiments, the layers may differ in their Brix.

Specifically, the soft coating binder solution may be characterized by its Brix value. In some embodiments, the soft coating binder solution is characterized by a Brix of between 60 to 70.

In some embodiments, the soft coating binder solution used for the first soft coating layer is higher than that used in subsequent layers of the soft coating (farther from the compressed core). For example, and without being limited thereto, the Brix of the binder solution used for forming the first layer of the soft coating is about 67 while that of the subsequent layers is about 62. The difference between the Brix is based on the desired outcome. While it has been found that 62 brix makes the outer layer more smooth and less rough, a higher brix of 67, used for the first layer dries faster. Thus, for allowing a faster drying of more internal soft coating layers, it is possible to use binder solutions with a Brix level closer to the higher end of the above identified range.

The layers are applied until a predetermined amount of gum base powder is applied onto the protected tablet and in other words, the desired thickness of the soft coating is produced.

In some embodiments, the gum base powder is applied until at least 700 gr gum powder is applied onto 1000 gr protected tablets.

In some embodiments, the soft coating step is repeated until at least 5, at times at least 10 and at times, at least 15 thin layers of the gum base powder containing layer are produced. In some embodiments, this gum base containing coating is performed until between 5 to 30 thin layers of the gum base powder, between 10 to 30 layers, and at times between 15 to 25 layers are applied.

In some embodiments, between one or more layers of the gum base powder and after the gum base has dried, the coated tablet is sprayed with an oil based material, typically, an oil based flavoring agent.

In some embodiments, the oil based material is sprayed over at least 1, at times, at least 2, 3, 4, 5 or more layers of the gum base powder.

In some embodiments, the application of the oil based agent is after every layer of the gum base powder, or every second layer, or every third layer or every fourth layer of the gum base powder.

In some embodiments, the application of the oil based agent is not in a fixed order of layers, but rather random, as long as there are at least three layers of the gum base powder that are sprayed with the oil based agent.

The soft (gum base) coated tablet may then be coated with additional layers as known in the tablet industry.

For example, the soft coated tablets may include, over the soft coating, a hard coating. Such hard coating may be obtained by applying one or more layers of a hard coating binder, the composition of the hard coating binder being as defined above.

In some embodiments, the layers of the hard coating are produced by sequential application of the hard coating binder in a drum, in a manner similar to that used for applying the soft coating binder. Specifically, the gum-base coated tablets are wetted with a solution of the hard coating binder, mixed within a drum and allowed to dry before application of a subsequent layer of the hard coating binder.

In some embodiments, the hard coating comprises also pigments, as described above. The pigments, such as titanium dioxide is mixed into the binder solution.

In some further embodiments, the tablets may be coated by a color coating over the hard coating. The application of the color coating may be in the same manner as the previous coats, i.e. by wetting the tablets with the color solution within a drum.

Finally, an in accordance with some embodiments, the coated tablets may be polished, typically by applying polishing material over the hard and optionally color coating.

Description of Non-Limiting Embodiments

Materials

Tablet: each tablet weighted 800 mg and contained sorbitol as the water soluble carrier/filler, magnesium stearate as the lubricant, and one or more of vitamins, minerals, plant derived parts, flavoring agents, all as described in Table 1 below.

TABLE 1

| Ingredient | Tablet #1: Ginger | Tablet #2: Multivitamin | Tablet #3: Herb |
|---|---|---|---|
| Sorbitol | 708.16 mg | 424.95 mg | 596.32 mg |
| Maltodextrin | 40.4 mg | — | — |
| Mg Stearate | 9.1 mg | 3.25 mg | 6 mg |
| Flavoring agent | — | 10.08 mg (Berries Flavor) | 32 mg (Orange Flavor) |
| Vitamins | Vitamin C-10 mg Vitamin B6-7.32 mg | Vitamin A-3.3 mg Vitamin D3-1.25 mg Vitamin E-10.01 mg Vitamin B1 1.53 mg Vitamin B2-2.03 mg Biotin-0.49 mg Vitamin B3-9.1 mg Vitamin C-25.01 mg Folic Acid-2 mg B12-0.01 | Vitamin C-50 mg |
| Minerals | — | Calcium Carbonate-132.44 mg Ferrous Fumarate 12.5 mg Mangan Sulfate-5.01 mg Chromium Picolinate-0.05 mg Zinc Oxide-7 mg | Zinc Oxide-10.67 mg |
| Herbs | Zingiber officinale-25.02 mg | — | berry-50 mg Astragalus-50 mg Licorice-50 mg |

The above tablet cores were coated with a protective coating or soft and hard coatings of different ingredients, as detailed below.

The protective coating included a cellulose based polymer (e.g. EC or HPMC) or wax based material (microcrystalline or bees wax and carnauba wax).

The soft and hard coating included different combinations of chewing gum powder, isomalt, gum Arabic, flavoring agents like Tutti Frutti, titanium dioxide (typically in the hard coating), coloring Agent, like black carrot and safflower extracts (also typically in or over the hard coating).

The layers external to the tablet core were identical, except for the coloring agent as described below.

Methods (a) Creating Tablets:

The ingredients of each tablet were sieved and mixed with the carrier, sorbitol, to form a fine mixture, to which the lubricant, Mg stearate, was added and further mixed until a homogenous mixture is obtained. The mixture was then subjected to tableting and dedusting (by conventional technique).

Tablet hardness was determined by Tablet hardness tester (VanderKamp® VK 200) and confirmed to be 9-12 Kilopond (the tablet needs to be soft enough to allow chewing yet hard enough to withstand the next steps within the drum coater without breaking or cracking).

(b) Providing a Protective Coating:

For protective coating, a solution of ethyl cellulose (AQUALON™ EC-N10) in ethanol 99% was prepared by dissolving 8 mg of EC in 72 μl and the resulting solution was sprayed onto the tablets when the latter rotated inside a drum. The ethanol evaporated to provide dry EC coated tablets ("EC-tablets"). Without being bound by theory, this EC layer prevents and protects each tablet from the infiltration of liquids and thus disintegration (see respective Figures described hereinbelow).

As reference/comparison, tablets without the protective coating were also formed as described hereinbelow.

(c) Providing Gumming Layers (Soft Coating)

Table 2 provides the composition of the gum (soft) coating.

TABLE 2

| Layer No. | Ingredient | Amount [mg] |
|---|---|---|
| 1 | Water (for isomalt solution) | 32.00 |
| 2 | Isomalt | 81.60 |
| 3 | Water (for Gum Arabic solution) | 64.80 |
| 4 | Gum Arabic | 43.20 |
| 5 | Flavoring agent ("tutti frutti") | 1.00 |
| 6 | Gum base powder | 640.00 |
| 7 | Strawberry flavor powder | 0.50 |
| 8 | Isomalt (for drying) | 4.76 |

To prepare the gum layers, an isomalt solution was prepared by adding isomalt to boiling purified water (1+2). When the solution turned clear (all isomalt dissolved), it was cooled.

In a separate container, Gum Arabic was added to purified water (at 70° C.) (3+4) while stirring. This solution was then left to settle for a number of hours, after which the foam was removed and the two solutions were mixed. This mixture constitutes the gum binding solution. The sugar concentration in the combined gum binding solution was 67 Brix, as measured by a refractometer.

Coating of the EC-core tablets was within a drum a priori exposed to the combined binding solution to create friction on the walls of the drum that would cause the tablet to rotate in the drum. Tablets (1 kg) were then placed inside the drum.

Separately the chewing gum powder was prepared by mixing gum base powder (6) with flavoring powder (7).

The first gumming layer was prepared by spinning the drum and adding thereto the binding solution (67 Brix). In subsequent layers the sugar concentration was reduced to 62 Brix while the amount of solution increased. After each addition of a volume of the combined binding solution, chewing gum powder was spread over the tablet and "glued" to the tablet by the combined binding solution (acted as a binder).

The gum coating ended when about 800 gram of chewing gum powder was used. The multi-layered gum tablets was then played on a tray for 24 hours (20° C.-25° C., 40% humidity) until reaching dryness.

It is noted that isomalt 8 is added when the product in the drum is too wet and the air dryer is not enough.

(d) Providing Hard "Crust" Coating Over the Soft Coating

First a crusting solution was prepared by adding isomalt to boiling purified water until complete dissolution of the isomalt (the formation of a clear solution). The clear solution was then cooled.

In a separate container, gum arabic was added to purified water (at 70° C.) while stirring. This solution was then left to settle for a number of hours, after which the foam was removed.

The two solutions were then combined and titanium dioxide dissolved in water was finally added to the combined solution.

The sugar concentration in the $TiO_2$-combined solution was 67 Brix, as measured by a refractometer. The concentration was measured prior to adding the $TiO_2$.

Coating of the multi-layered gum tablets was within a drum a priori exposed to the combined solution to create friction on the walls of the drum that would cause the tablet to rotate in the drum.

Tablets were then placed inside the drum and while spinning the drum, the $TiO_2$-combined solution was gradually added, in batch amounts, each amount until wetting the tablets, yet, without flooding the drum. Between each addition, sufficient time was allowed to bring the tablets to dryness, each addition thus forming a thin layer of a crust coating.

After about 20 rounds of coating (formation of 20 layers), the crusted tablets were removed and placed on a drying tray for 24 hours (20° C.-25° C., 40% humidity) until reaching dryness.

Table 3 provides the ingredients used for preparing the hard coating

TABLE 3 hard (crust) coating

| Ingredient | Amount [mg] |
|---|---|
| Water (for gum arabic) | 26.00 |
| Gum Arabic | 17.28 |
| Isomalt | 270.00 |
| Liquid Flavoring agent (strawberry) | 0.88 |
| Water (for isomalt) | 118.80 |
| Titanium dioxide | 10.80 |
| Water (for titanium dioxide) | 10.80 |

(e) Providing Color Coating

First a coloring was prepared by adding isomalt (270 mg) to boiling purified water until complete dissolution of the isomalt (the formation of a clear solution). The clear solution was then cooled.

In a separate container, gum arabic (17.28 mg) was added to purified water (at 70° C.) while stirring. This solution was then left to settle for a number of hours, after which the foam was removed.

The two solutions were then combined and titanium dioxide dissolved in water and coloring agent, like black carrot and safflower extracts were finally added to the combined solution. It is to be noted that concentrations may vary depending on the color of interest.

The sugar concentration in the combined coloring solution was 67 Brix, as measured by a refractometer.

As conducted with previous layers, coating of the multi-layered gum tablets was within a drum a priori exposed to the combined coloring solution to create friction on the walls of the drum that would cause the tablet to rotate in the drum.

The crust-coated tablets were then placed inside the drum and while spinning the drum, the combined coloring solution was gradually added, in batch amounts, each amount until wetting the tablets, yet, without flooding the drum. Between each addition, sufficient time was allowed to bring the tablets to dryness, each addition thus forming a thin layer of a color coating.

After about 10 rounds of coating (formation of 10 layers), the crusted tablets were removed and placed on a drying tray for 24 hours (20° C.-25° C., 40% humidity) until reaching dryness.

The coloring agent used in the various exemplary coated tablets:

Ginger containing tablet—Safflower extract
Multivitamin containing tablet—Black Carrot extract
Herbs containing tablet—Black Carrot extract (f) Polishing For polishing of the colored tablets, metal baffles were placed in the drum along with microcrystalline wax and carnauba wax used as polishing agents. The drum was then spin at high speed (25-35 RPM) for about 20 minutes.

Results

Various types of tablets were formed, being different in the tablet core, while the coating layers were identical (yet with or without the intermediate, protecting coating).

Generally, it has also been found that the protective (EC based) coating stabilizes the product, i.e. significantly prevents/protects the outer coating from cracking.

In addition, it has been found that spraying of the coated tablets with an oil based flavoring agent, the resulting product was softer in comparison to the same product that was not oil sprayed (not described).

Ginger Containing Tablets

Figure 2:
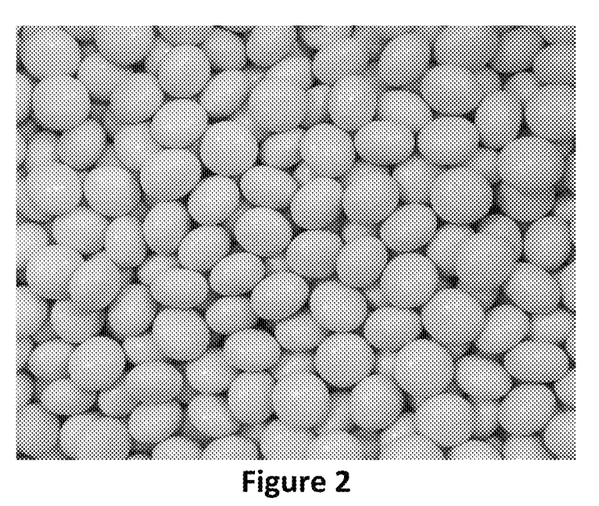
FIG. 2 is a photographic images of Ginger containing tablets (core tablet #1 in Table 1) obtained in accordance with the present disclosure.

FIG. 2 is a photographic image of ginger containing tablets taken 12 months after storage at 25° C.

As seen, the yellow tablets have no visible cracks or chips on their surface, indicating that the coated tablet is storage stable.

It has also been found that the spraying of the coated tablets with an oil based flavoring agent, the resulting product was softer in comparison to the same product that was not oil sprayed (not described).

FIG. 3A-3D are photographic images of tablets with or without the EC based protective coating and all being absent of the additional layers (e.g. the soft coating and/or hard coating provided over the protective coating).

Figure 3A:
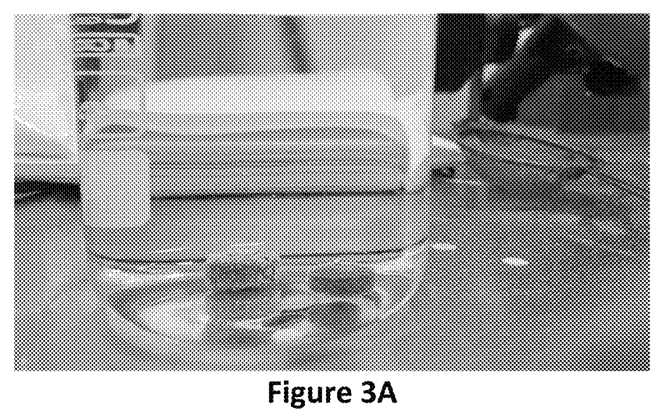
FIGS. 3A-3D are photographic images, at different time points, of berries+Vitamin C-containing tablets (core tablet #3 in Table 1) with EC protective coating (Right side tablet) or without the EC based protective coating (left side tablet) and without the additional layers (provided after the protective coating) after being placed in water, where
Figure 3B:
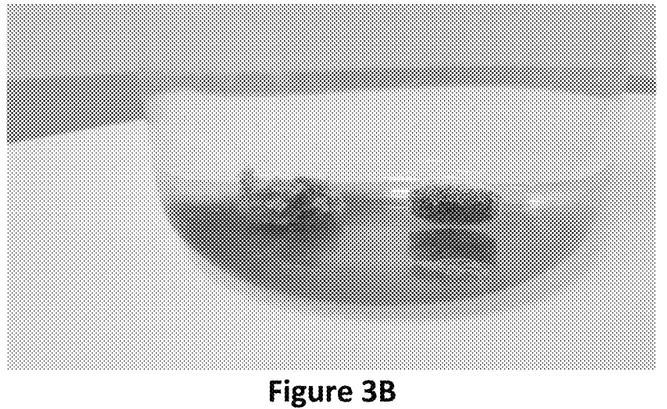
Figure 3C:
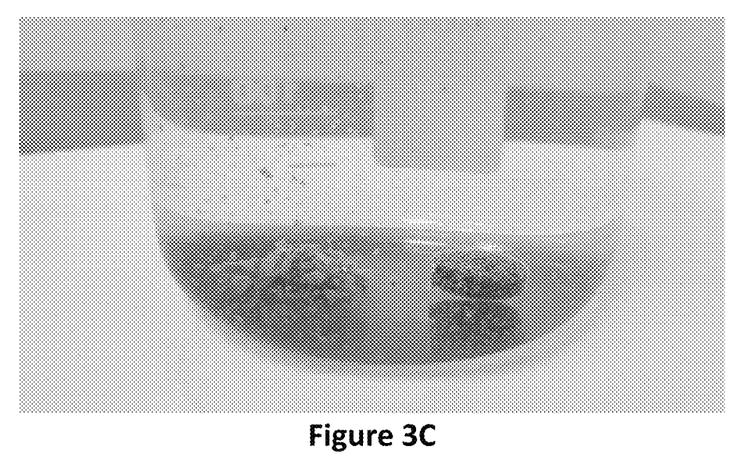
Figure 3D:
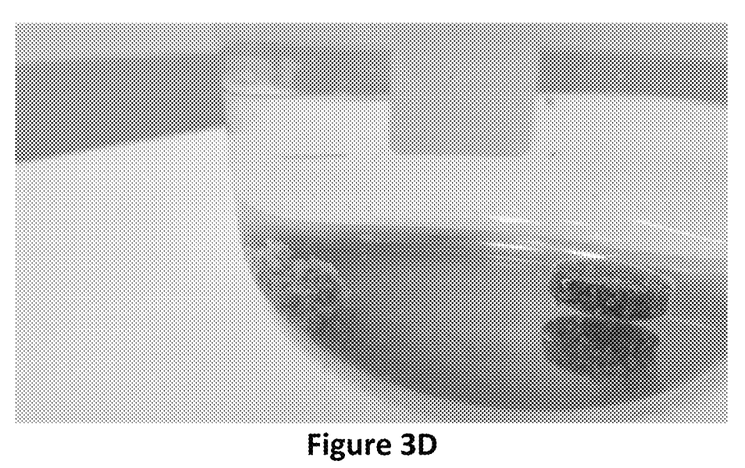

FIG. 3A is taken immediately after insertion into water, FIG. 3B is taken 4 hours after insertion into the water, FIG. 3C is taken 18 hours after insertion into the water, and FIG. 3D is taken 24 hours after insertion into the water.

FIGS. 3A-3D clearly show that in time, the tablets including the protective EC protective coating do not disintegrate, i.e. are stable in water.

Child Tablets

Figure 4A:
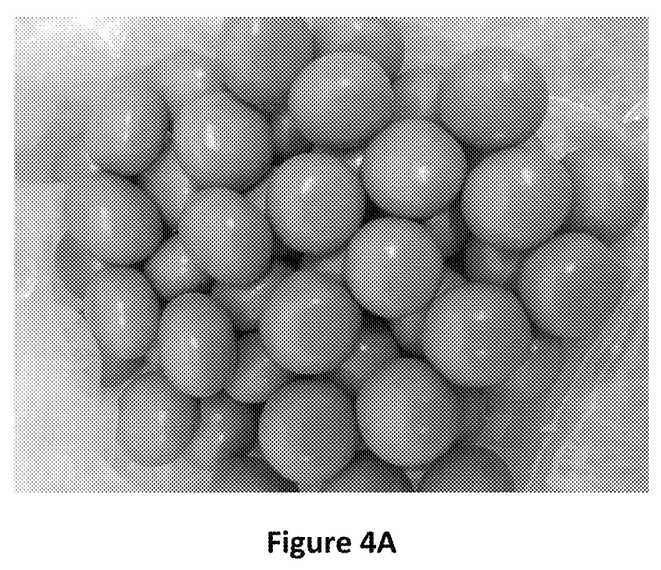
FIGS. 4A-4B are photographic images of tablets (core tablet #3 in Table 1) with a protective layer (FIG. 4A) or without a protective layer (FIG. 4B), the images taken 1 year after production.
Figure 4B:
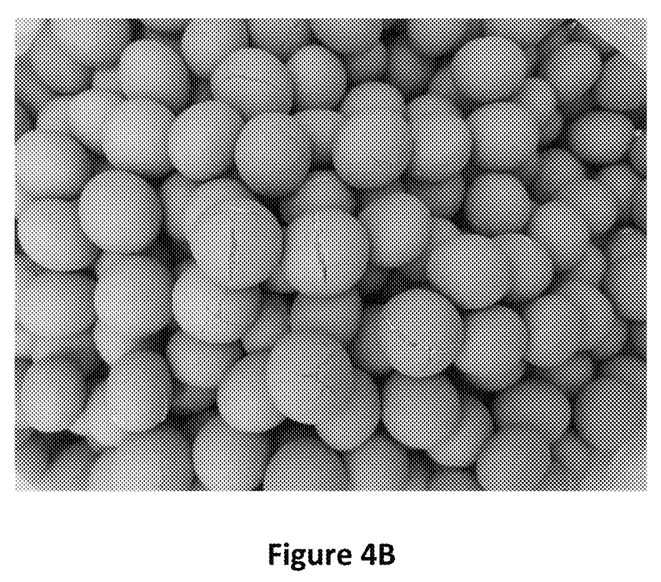

FIG. 4A is a photographic image of tablets produced with herb containing core tablet (Tablet 3, from Table 1), and EC protective coating, taken 1 year after production. In comparison, FIG. 4B is a photographic image of tablets produced in the same manner, yet, without the protective (EC) sprayed layer.

As seen, the pink tablets have no visible cracks or chips on their surface when including the protective coating (FIG. 4A), indicating that the coated tablet is storage stable.

In the absence of the protective layer, cracks appeared on the outer surface after I year when stored at the same storage conditions as with the tables shown in FIG. 4A. This is shown in FIG. 4B and clearly support the necessity of the protective layer for maintaining integrity of the tablets.

Multi-Vitamin Tablets

Figure 5:
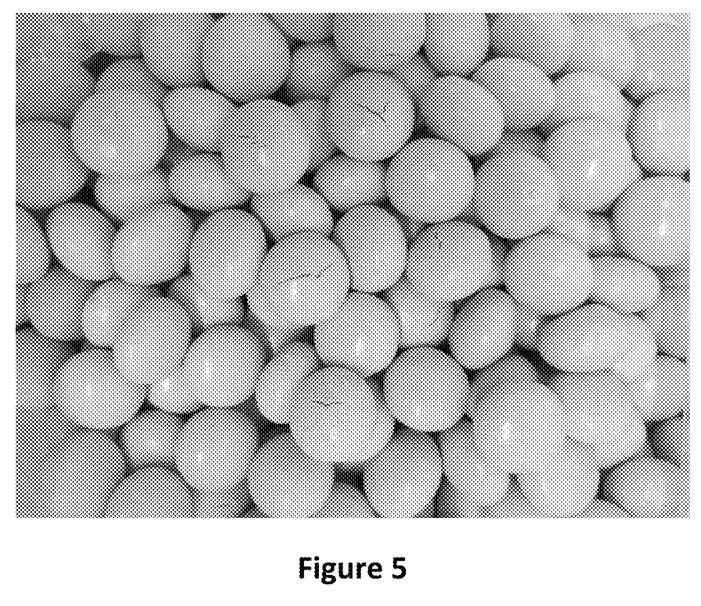
FIG. 5 is a photographic image of gum coated multi-vitamin tablets (core tablet #2 in Table 1) without a protective layer, after storage.

FIG. 5 is a photographic image of multi-vitamin-containing tablets (core tablet #2 from Table 1) that do not include the EC protective layer. The image is taken 1 year after production.

As with the ginger tablets and herb tablets (core from Table 1), the presence of the EC protective coating was found to be crucial for maintaining integrity of the tablets after storage.

Based on the above results it is evident that the protective coating, acting, inter alia, as a barrier, protects the tablet during storage and thus is essential, especially for large scale, commercial production.

COMPARATIVE EXAMPLES

To further emphasize the non-obvious selection of ethyl cellulose based protective coating, vitamins containing core tablets (as core tablet 2 from Table 1) were prepared as described above and were coated with hydroxypropyl methylcellulose in the same manner as described above for Ethocel or with Bees wax (first liquified at 60° C.) or Carnauba wax (applied as powder). None of these protective layers successfully prevented disintegration of the coated tablet once placed in water, this being in complete contradiction to the results presented in FIGS. 4A-4B for Ethocel coating.

Figure 6A:
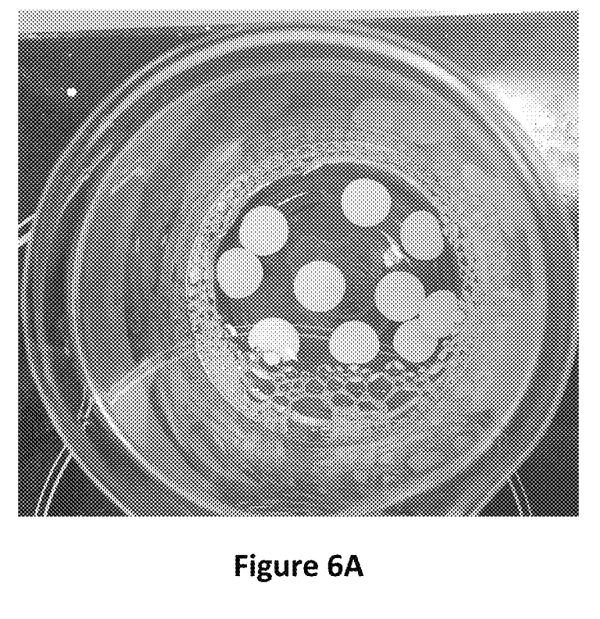
FIGS. 6A-6E are photographic images, at different time points, of Vitamins containing tablets (core tablet #2 of Table 1) with or without a protective coating, where
Figure 6B:
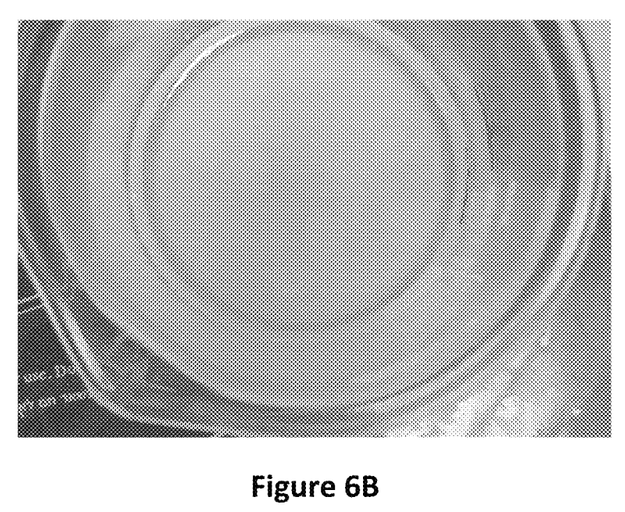
Figure 6C:
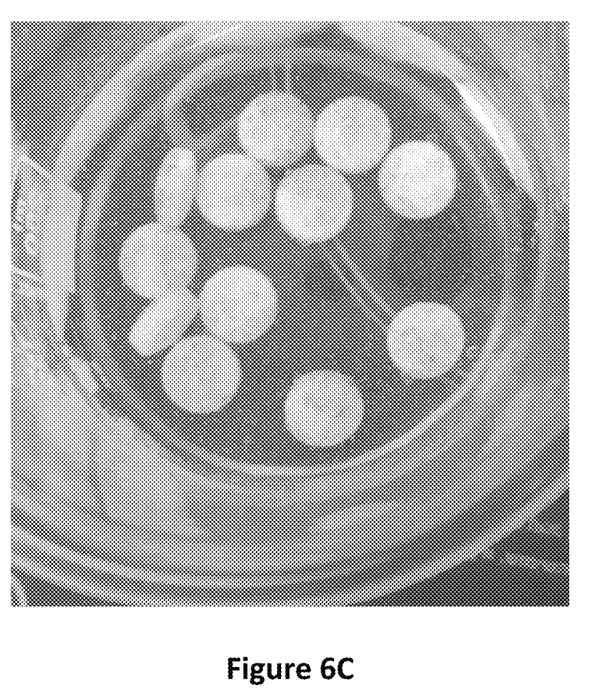
Figure 6D:
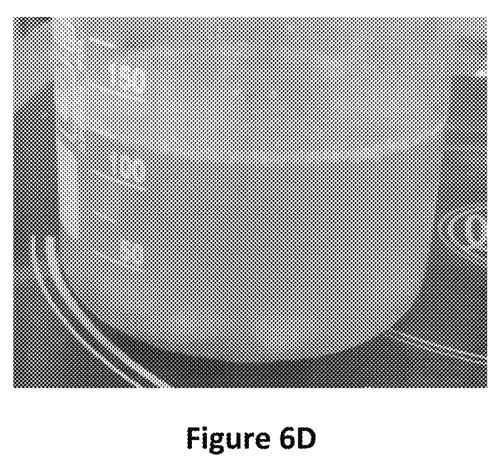
Figure 6E:
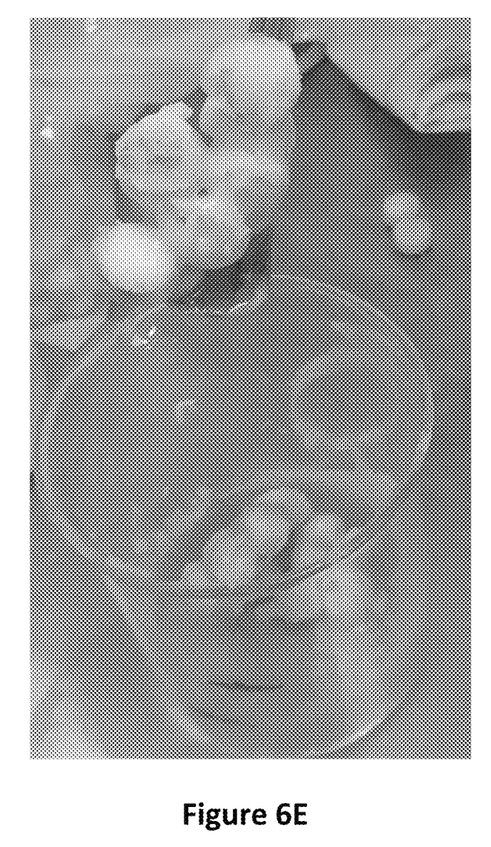

Specifically, FIG. 6A-6B show the disintegration of HPMC coated tablets, already after 40 minutes in water; FIGS. 6C-6D show the disintegration of carnauba was-coated tablets, already after 20 minutes in water and FIG. 6E show that it was impossible to coat vitamin tablets with bees wax as the melting of the wax damaged the compressed core tablet.

The invention claimed is:

1. A chewable tablet comprising
a compressed core including a bioactive molecule;
a protective layer over the compressed core,
   wherein the protective layer comprises a water-insoluble cellulose based polymer; and
two or more soft-coating layers over the said protective layer,
   wherein each soft coating layer comprises gum base powder,
   wherein an innermost layer of the two or more soft coating layers is bound to the protective layer,
   wherein the chewable tablet comprises a sufficient amount of the water-insoluble cellulose based polymer in the protective layer to result in, when tested after 12 months of storage at 25° C., the chewable tablet not disintegrating 24 hours after insertion into water.

2. The chewable tablet of claim 1, wherein said protective layer comprises ethyl cellulose.

3. The chewable tablet of claim 2, wherein said protective layer consists essentially of ethyl cellulose and optionally residual organic solvent.

4. The chewable tablet of claim 1, wherein said compressed core is a compressed tablet having a hardness of between 9-12 kilopond.

5. The chewable tablet of claim 1, comprising between 10 to 25 layers of said gum base powder.

6. The chewable tablet of claim 1, wherein each of said soft coating layers comprises a soft coating binder for binding said gum base powder to the protective layer or to a preceding soft coating layer.

7. The chewable tablet of claim 6, wherein said soft coating binder comprises a sugar-based material and gum Arabic.

8. The chewable tablet of claim 1, wherein said soft coating layers comprise an oil-based agent between two or more soft coating layers.

9. The chewable tablet of claim 1, further comprising a hard-coating comprising a hard coating binder over said two or more soft-coating layers.

10. The chewable tablet of claim 9, wherein said hard-coating binder comprises a sugar-based material and gum Arabic.

11. A method of preparing a chewable tablet comprising:
(a) applying a protective material onto a compressed tablet comprising a bioactive molecule, the protective material comprising a water-insoluble cellulose based polymer to form a protective layer on said compressed tablet;
(b) applying two or more soft-coating layers onto said protective layer, said two or more soft coating layers comprising gum base powder, wherein an innermost layer of said two or more soft coating layers is applied to said protective layer,
wherein the chewable tablet comprises a sufficient amount of the water-insoluble cellulose based polymer in the protective layer to result in, when tested after 12 months of storage at 25° C., the chewable tablet not disintegrating 24 hours after insertion into water.

12. The method of claim 11, wherein said applying of (a) comprises spraying said polymer over the compressed tablet when said polymer is dissolved in an organic solvent.

13. The method of claim 11, wherein said water insoluble polymer is ethyl cellulose.

14. The method of claim 12, wherein said organic solvent is ethanol.

15. The method of claim 14, wherein said ethanol is ethanol 99%.

16. The method of claim 12, comprising evaporating the organic solvent prior to applying the two or more soft-coating layers of (b).

17. The method of claim 11, wherein applying the two or more soft-coating layers of (b) comprises wetting the compressed tablet resulting from (a) with a soft coating binder solution and spreading over said wet tablets gum base powder.

18. The method of claim 17, wherein said soft coating binder solution comprises a sugar based material and gum Arabic dissolved in water.

19. The method of claim 11, wherein applying said two or more soft-coating layers of (b) comprises introducing gum base powder into a drum while mixing therein wet tablets resulting from (a), thereby forming a layer of the gum base powder over the tablet, and drying the layer of gum base powder before applying an additional soft coating layer.

20. The method of claim 19, wherein said introducing gum base powder into a drum while mixing the tablets therein is repeated between 10-25 times to obtain a soft coating comprising 10-25 layers of said gum base powder.

21. The method of claim 11, comprising applying an oil based agent between at least two of said two or more soft coating layers.

22. A chewable tablet comprising:
a compressed core including a bioactive molecule;
a protective layer over the compressed core,
   wherein the protective layer comprises water-insoluble cellulose based polymer; and
two or more soft-coating layers over the protective layer,
   wherein each soft coating layer comprises gum base powder,
   wherein an innermost layer of the two or more soft coating layers is directly bound to the protective layer,
   wherein the water-insoluble cellulose based polymer comprises ethyl cellulose in an amount, out of a total amount of polymers in the protective layer, that is not less than 40% by weight.

\* \* \* \* \*